(12) United States Patent
Shiba et al.

(10) Patent No.: US 7,776,264 B2
(45) Date of Patent: Aug. 17, 2010

(54) AUTOMATIC ANALYZER

(75) Inventors: Masaki Shiba, Hitachinaka (JP);
Hideyuki Yanami, Hitachinaka (JP);
Masaharu Nishida, Hitachinaka (JP);
Hitoshi Ohtake, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 758 days.

(21) Appl. No.: 11/033,383

(22) Filed: Jan. 12, 2005

(65) Prior Publication Data

US 2005/0175503 A1 Aug. 11, 2005

(30) Foreign Application Priority Data

Jan. 28, 2004 (JP) ............................. 2004-019142

(51) Int. Cl.
*G01N 35/00* (2006.01)
*G01N 35/02* (2006.01)

(52) U.S. Cl. ..................................... 422/67; 422/82.05

(58) Field of Classification Search ............ 422/63–67, 422/100, 68.1; 436/43–49, 50
See application file for complete search history.

(56) References Cited

U.S. PATENT DOCUMENTS

| | | | | |
|---|---|---|---|---|
| 4,451,433 A | * | 5/1984 | Yamashita et al. | ............ 422/63 |
| 4,774,055 A | * | 9/1988 | Wakatake et al. | ............ 422/64 |
| 5,125,748 A | * | 6/1992 | Bjornson et al. | ............ 356/414 |
| 5,254,311 A | | 10/1993 | Ushikubo | |
| 5,827,479 A | | 10/1998 | Yamazaki et al. | |

FOREIGN PATENT DOCUMENTS

| | | |
|---|---|---|
| EP | 0845674 | 6/1998 |
| JP | 10-142230 | 5/1998 |

* cited by examiner

*Primary Examiner*—Jill Warden
*Assistant Examiner*—Cedric Chan
(74) *Attorney, Agent, or Firm*—Mattingly & Malur, P.C.

(57) ABSTRACT

An automatic analyzer capable of replenishing a reagent even during an analysis and minimizing a suspension of the analysis. The automatic analyzer includes a plurality of reaction cells and a unit for holding reagents used in analyses. A plurality of reagents are dispensed to a sample in each reaction cell with a time difference to develop a reaction, and a liquid after the reaction is measured. After temporarily stopping the operation of dispensing the sample for a preset time during the analysis, the sample dispensing operation is restarted. Then, the sample dispensing operation is temporarily stopped again for the preset time at the timing in the dispensing of the reagent corresponding to the timing at which the sample dispensing operation was temporarily stopped. In the automatic analyzer, therefore, an analysis suspension due to registration and replacement of reagents during the analysis can be minimized, a larger number of reagents can be loaded, and a throughput per unit time can be increased.

8 Claims, 8 Drawing Sheets

AUTOMATIC ANALYZER

BACKGROUND OF THE INVENTION

1. Field of the Invention

The present invention relates to an automatic analyzer for performing qualitative and quantitative analyses of living samples, such as blood and urine, and more particularly to an automatic analyzer having a larger number of reagents placed per unit area.

2. Description of the Related Art

In an automatic analyzer for performing qualitative and quantitative analyses of living samples, such as blood and urine, the analysis is generally performed through the steps of adding, to each of the living samples, a reagent that reacts with a particular component in the sample to change a sample color, and measuring a change of the sample color (i.e., a change of absorbance) by using a photometer or the like.

In such an automatic analyzer, reagents required for the measurement are placed in the analyzer before the sample analysis is started. Recently, with improvements of reagents, the number of analysis items measurable by the automatic analyzer has increased, and the number of kinds of reagents has increased correspondingly.

For that reason, there is a demand for increasing the number of reagents capable of being placed in the automatic analyzer. On the other hand, space saving of the automatic analyzer is also demanded. In the past, a reagent bottle having a volume in match with the quantity of the reagent, which is estimated to be consumed in a day, so that once the reagent is replaced with a new one in the morning of everyday, it is possible to avoid the reagent from being used up in the day and to eliminate the necessity of replacing the reagent bottle. However, when the volume of each reagent bottle is reduced to increase the number of reagents capable of being placed in the automatic analyzer, this increases a possibility that the reagent runs out in some reagent bottle during the analysis. Accordingly, there is a demand for the function capable of smoothly replacing the reagent bottle even during the analysis.

Patent Reference 1; JP,A 10-142230 discloses such a technique that sample dispensing or subsequent reagent sampling can be temporarily stopped by an operator depressing a "reagent registration interrupt" key on an analyzer control screen when the amount of the remaining reagent has become small during the analysis. Because the reagent can be replenished or replaced during the analysis, the reagent is just required to be placed in a necessary minimum amount. It is therefore possible to provide an analyzer in which the reagent can be replenished or replaced even when the reagent has run out, and to realize space saving of the analyzer.

SUMMARY OF THE INVENTION

Although the technique disclosed in Patent Reference 1 is able to stop the dispensing of the sample, the dispensing of the reagent cannot be stopped until the end of the analysis for a reaction cell in which the sample has already been dispensed. In the case of an analysis item based on a 2-liquid reaction using R1 (first reagent: i.e., a reagent added immediately after the sample has been dispensed into the reaction cell) and R2 (second reagent: i.e., a reagent dispensed after about 5 to 10 minutes from the dispensing of the first reagent), the operation of dispensing the reagent is actually stopped after R2 has been completely dispensed to all reaction cells in which the samples have already been dispensed. Thus, a wasteful waiting time occurs. Further, samples cannot be dispensed during not only such a waiting time, but also a time required for replacing the reagent. This leads to a problem of taking a longer time until the sample analysis is resumed after replacing the reagent.

It is an object of the present invention to provide an automatic analyzer with the function of minimizing a reduction in an analysis speed even when the necessity of replacing a reagent occurs.

To achieve the above object, the present invention is constructed as follows.

The automatic analyzer of the present invention comprises a reaction cell for mixing a sample and at least one reagent therein; a sample dispensing unit for dispensing the sample into the reaction cell; a reaction cell carrying unit for holding the reaction cell in plural number and successively carrying the reaction cells at constant timing; a reagent dispensing unit for drawing a reagent from a reagent bottle and injecting the drawn reagent into the reaction cell on the reaction cell carrying unit at predetermined timing; and a control unit for, when the reagent bottle for supplying the reagent to the reagent dispensing unit is replaced, controlling the sample dispensing unit such that sample dispensing operation of the sample dispensing unit is stopped for a preset time required for the reagent replacement at a point in time prior to the reagent replacement by a period taken from the dispensing of the sample to timing of adding the reagent to the dispensed sample.

The reaction cell carrying unit is constituted, for example, as a mechanism of rotating a turntable on which a plurality of reaction cells are arranged along a circumference thereof, or as a mechanism of conveying a belt on which a plurality of reaction cells are arranged. Also, a path along which the reaction cells are transported is not limited to the form of a loop, but it may have the linear form. The expression "constant timing" means that the reaction cells are repeatedly moved and stopped at a predetermined cycle. While the reaction cells are in the stopped state, samples and reagents are dispensed into the reaction cells.

With the procedure of stopping the sample dispensing operation of the sample dispensing unit for the preset time required for the reagent replacement and then restarting the sample dispensing operation, an analysis suspension time can be minimized (i.e., restricted to only a time required for the reagent replacement), and hence a reduction in analysis processing efficiency can be suppressed in comparison with the technique disclosed in Patent Reference 1. At the time of the reagent replacement, the dispensing of the reagent by the reagent dispensing unit should be stopped to avoid interference with the operation of replacing the reagent bottle. Typical examples of the reagent dispensing unit are of the so-called dispenser type that a tube is connected to the reagent bottle and the reagent is sucked in a required amount, and of the so-called pipetter type that a dispensing (pipetting) probe is descended into the reaction cell to suck the reagent in a required amount. If such a reagent dispensing unit is actuated for the reagent replacement during the analysis operation, there may arise a possibility, for example, that the reagent is dispensed in an improper amount, or the dispensing probe hits and hurt the operator in the operation of replacing the reagent.

The expression "injecting the drawn reagent into the reaction cell on the reaction cell carrying unit at predetermined timing" means injection of a first reagent (Reagent 1; R1) that is added immediately after dispensing the sample, and injection of a second reagent (R2), a third reagent (R3), a fourth reagent (R4), etc. which are added thereafter. The timings of injecting the second and subsequent reagents (R2, etc.) are decided beforehand depending on the reagents to be, for example, 3 minutes, 5 minutes, etc. after the dispensing of R1. Further, only R1 and R3 are added in some of analysis items, while R1, R2 and R3 are all added in other analysis items.

The expression "at a point in time prior to the reagent replacement by a period taken from the dispensing of the sample to timing of adding the reagent to the dispensed sample" means that, in spite of the operator instructing the analyzer to stop for the reagent replacement at a current point in time, the reagent replacement cannot started at once and a message indicating a reagent replaceable state is displayed after the lapse of a time required from the dispensing of the sample at the current time to the timing of adding the relevant reagent, thereby informing the operator of the reagent replaceable state. Accordingly, even if the necessity of the reagent replacement is confirmed at the current point in time, the analyzer of the present invention is adaptable for that necessity only after the ongoing analysis operation is suspended.

In view of that point, it is preferable to estimate the timing of the reagent replacement for more prompt and precise adaptation. One preferable example of the method for estimating the timing of the reagent replacement is to provide a remaining-reagent amount monitoring unit and to previously decide, for example, a rule of "replacing the reagent in any case after 10 minutes from a point in time at which the amount of the remaining reagent has reached a certain level". Another preferable example is to estimate, through predictive calculations based on information regarding the amount of the remaining reagent and the analysis items registered in the automatic analyzer to be analyzed from then, at what point in time the timing of the reagent replacement is reached from the current time.

According to the present invention, as described above, the analysis stop (suspension) time required for the reagent replacement can be minimized by temporarily stopping the dispensing of the sample and the dispensing of the reagent only for the preset time. It is therefore possible to provide an automatic analyzer in which a time loss with the reagent replacement is small even when the reagent is going to run out during the analysis, and a multi-item analysis can be performed while realizing space saving.

DESCRIPTION OF THE PREFERRED EMBODIMENTS

Figure 1:
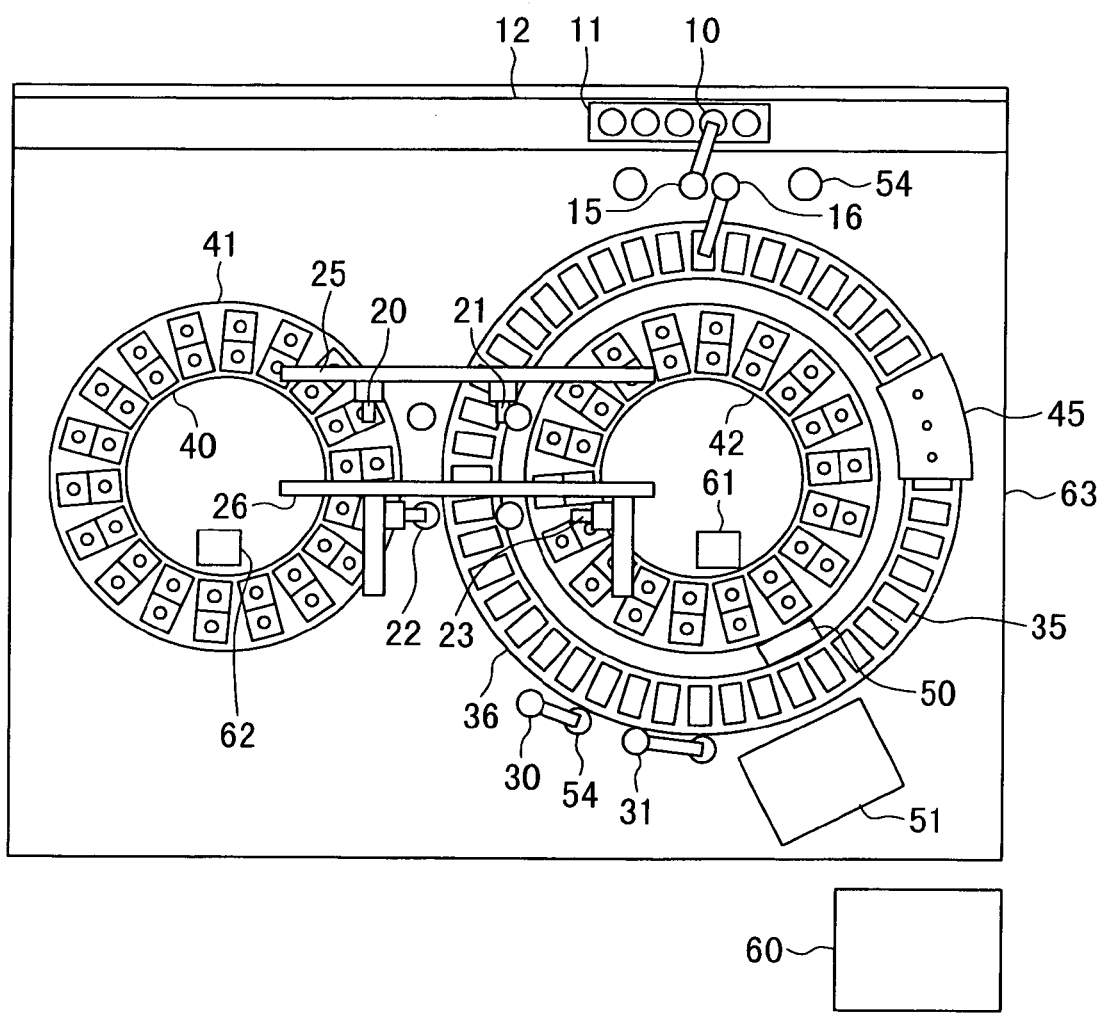
FIG. 1 is a plan view of an automatic analyzer according to a first embodiment of the present invention.

Embodiments of the present invention will be described below with reference to the drawings. FIG. 1 is a plan view of an automatic analyzer according to a first embodiment of the present invention. A plurality of reaction cells 35 are arranged along a circumference of a reaction disk 36 mounted on a casing 63. A reagent disk 42 is disposed inside the reaction disk 36, and a reagent disk 41 is disposed outside the reaction disk 36. A plurality of reagent bottles 40 can be placed along a circumference of each of the reagent disks 41, 42. One reagent bottle 40 is able to contain two kinds of reagents. A transport mechanism 12 for moving a rack 11, which holds a plurality of sample cups 10 thereon, is installed near the reaction disk 36. Rails 25, 26 are disposed to extend over the reagent disks 41, 42. Reagent probes 20, 21 capable of moving in the direction parallel to the rail 25 and in the vertical direction are mounted to the rail 25, and reagent probes 22, 23 capable of moving in the 3-axis directions with respect to the rail 26 are mounted to the rail 26. The reagent probes 20, 21, 22 and 23 are each connected to a reagent pump (not shown). Sample probes 15, 16 capable of rotating and moving in the vertical direction are disposed between the reaction cells 35 and the transport mechanism 12. The sample probes 15, 16 are each connected to a sample pump (sample syringe, not shown). Stirrers 30, 31, a light source 50, an optical detector 51, and a cell cleaning mechanism 45 are arranged around the reaction disk 36. The cell cleaning mechanism 45 is connected to a cleaning pump (cleaning syringe, not shown). Cleaning ports 54 are disposed in respective areas where the sample probes 15, 16, the reagent probes 20, 21, 22 and 23, and the stirrers 30, 31 are operable.

A reagent registering procedure using the automatic analyzer thus constructed will be described below.

A barcode is attached to each of the reagent bottles 40. An operator places the reagent bottle 40 on the reagent disk 41 or 42 after opening a cover (not shown) of the reagent disk 41 or 42. After the placement of reagents used for an analysis, when the analyzer recognizes that the operator has closed the cover (not shown) of the reagent disk 41 or 42, the analyzer automatically executes the reagent registering procedure by recognizing the barcode attached to the reagent bottle 40 with a barcode reader 61 or 62 which is disposed respectively aside the reagent disk 41 or 42. An analysis procedure using the analyzer of this embodiment will be described below.

The following description is made in accordance with a 2-reagent analysis method (i.e., an analysis method of dispensing two kinds of reagents into a sample with a time difference between them to develop a reaction).

A sample to be inspected, e.g., blood, is put in the sample cup 10 and is transported by the transport mechanism 12 while being set on the rack 11. A certain amount of the sample sucked by the sample probe 15 is dispensed into one of the reaction cells 35 arranged on the reaction disk 36, and a certain amount of a first reagent is dispensed into the reaction cell 35 from one of the reagent bottles 40 placed on the reaction disk 41 or 42 by using the reagent probe 21 or 22. The mixture in the reaction cell 35 is then stirred by the stirrer 30 or 31. After the lapse of a predetermined time, a certain amount of a second reagent is dispensed into the reaction cell 35 from another reagent bottle 40 placed on the reaction disk 41 or 42 by using the reagent probe 21 or 22, followed by stirring again by the stirrer 30 or 31. After the reaction for a predetermined time, the sample absorbance is measured by the optical detector 51, and the measured result is outputted to a control computer 60. If there remains one or more other measurement items requested, the above-described sampling process is repeated. For all the samples set on the rack 11, the sampling process is similarly repeated until all the set measurement items are completed.

One example of a procedure for replenishing reagents during the analysis in the automatic analyzer of this embodiment will be described below with reference to FIGS. 2 to 5.

Figure 2:
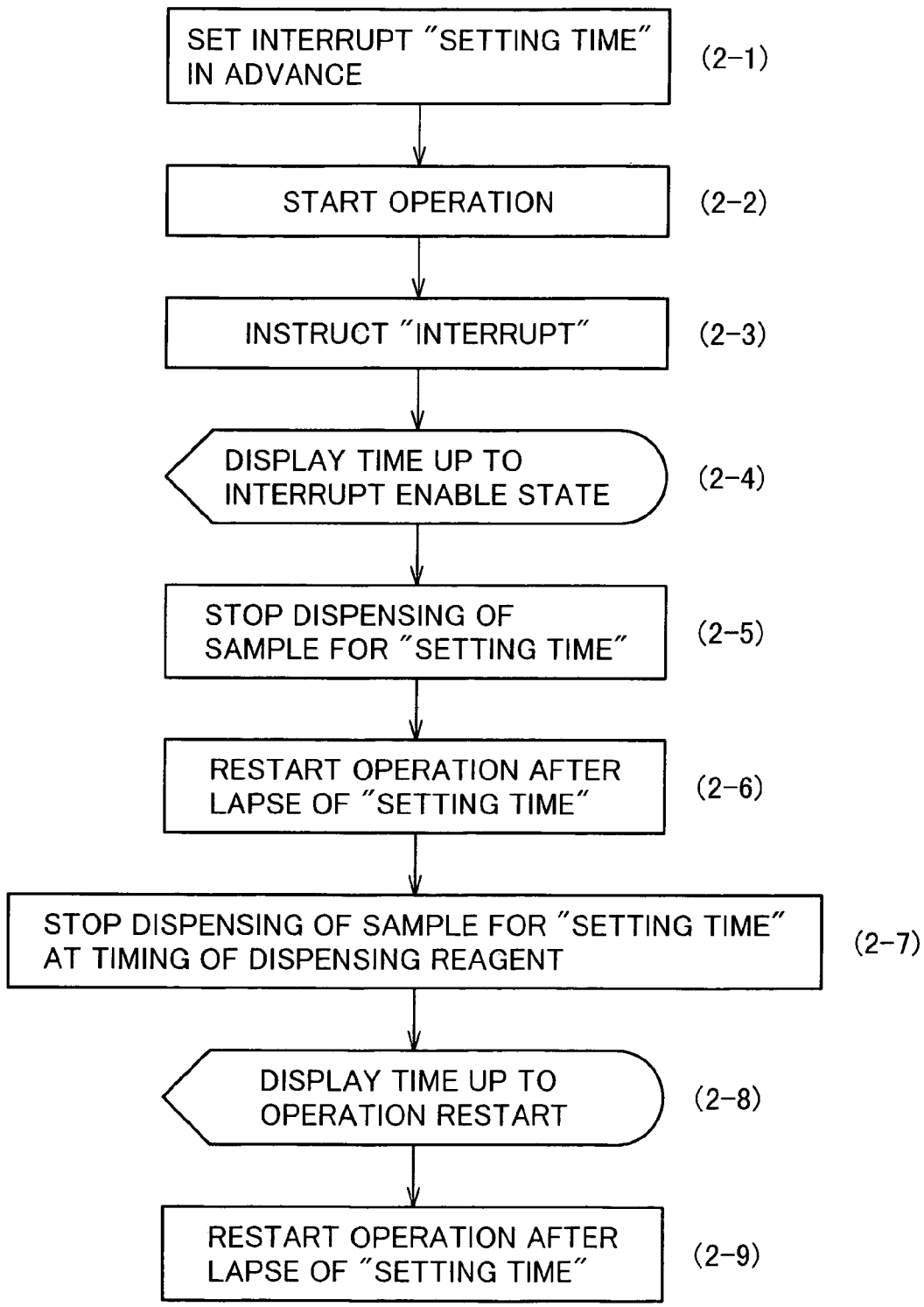
FIG. 2 is a flowchart for replenishing reagents in a 2-reagent analysis according to the first embodiment.

In this example, an interrupt time for replenishing reagents is set before the start of the analysis (operation) ((2-1) in FIG. 2). Note that the setting of the interrupt time is not always required to be registered before the start of the analysis, but the setting may be performed at any desired point in time before the timing of an interrupt for replenishing reagents.

Then, the analysis (operation) is started ((2-2) in FIG. 2). When it is desired to replenish one or more reagents during the analysis, the operator depresses a "reagent registration interrupt" button on an analyzer control screen, thereby issuing an "interrupt" command ((2-3) in FIG. 2 and FIG. 4). The button for issuing the "interrupt" command is not always required to locate on the control screen, but it may be disposed on the analyzer. In response to the button depression, the analyzer temporarily stops the dispensing of the sample for the preset "setting time" (sampling stop state) as indicated by (3-2) in FIG. 3. Simultaneously, the analyzer displays a "time up to reagent replenishment enable state" (FIG. 4), i.e., a time up to the timing at which the replenishment of the reagents will be enabled, as shown in FIG. 4.

Figure 3:
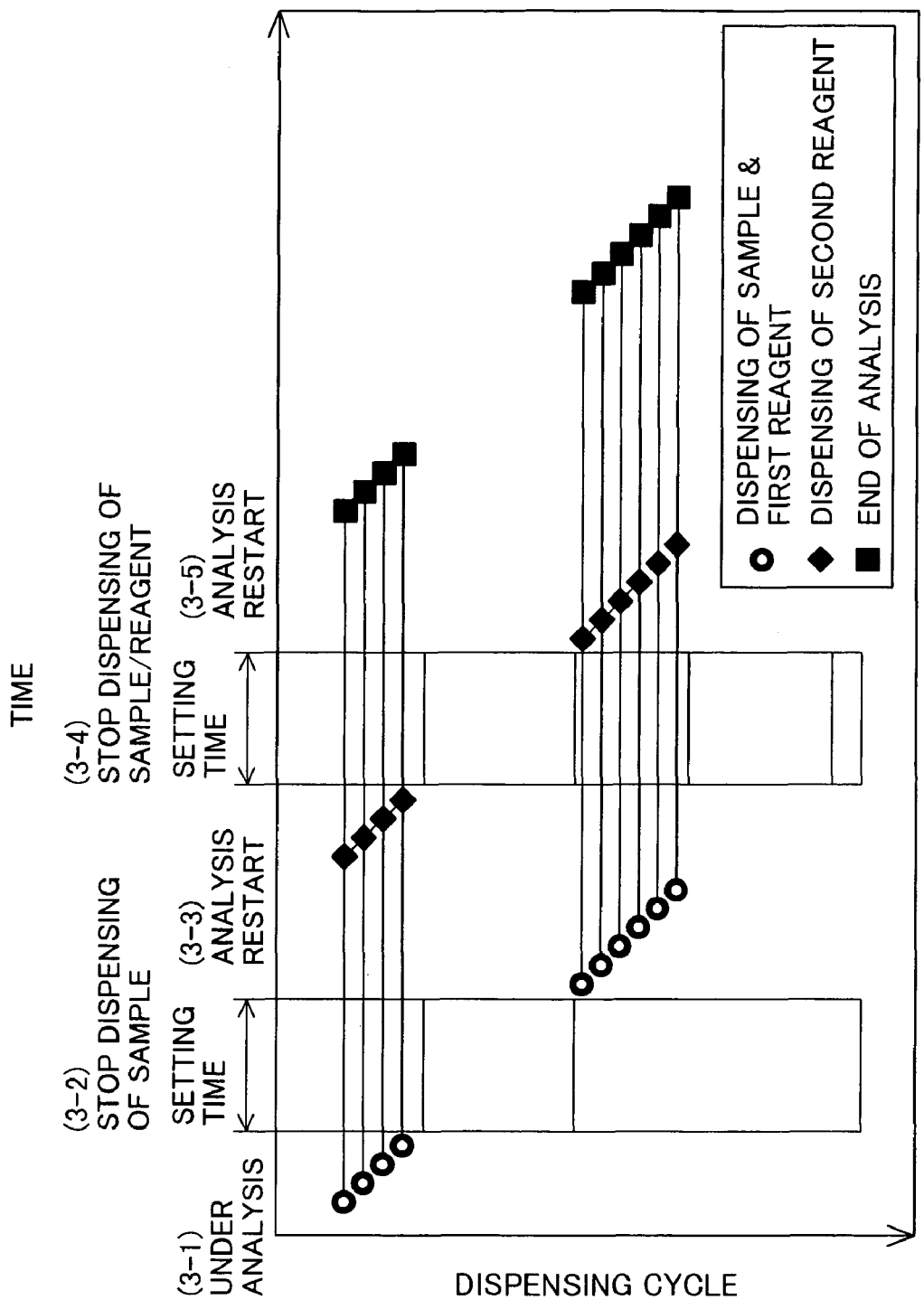
FIG. 3 shows a procedure for dispensing a sample and reagents in the 2-reagent analysis according to the first embodiment.
Figure 4:
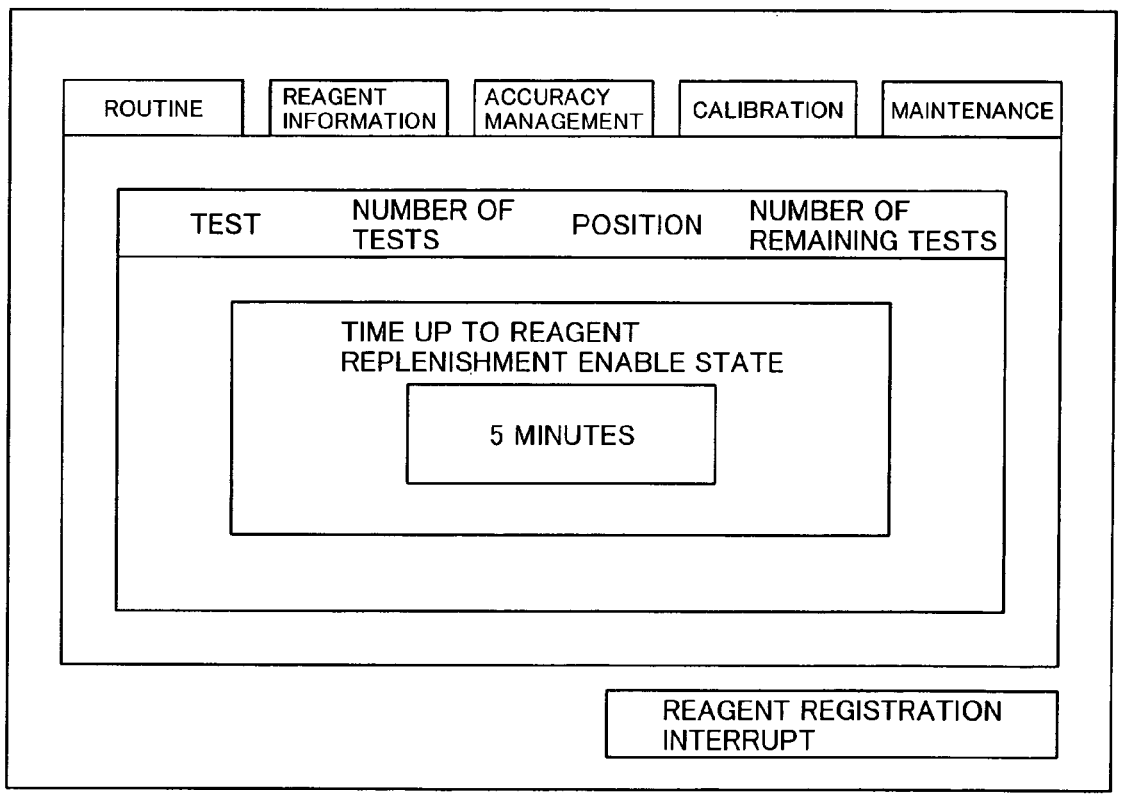
FIG. 4 shows a control screen 1 used in the first embodiment.

After the lapse of the "setting time", the analyzer restarts the dispensing of the sample ((2-6) in FIG. 2 and (3-3) in FIG. 3). Subsequently, at the timing in the dispensing of the second reagent corresponding to the timing at which the dispensing of the sample was temporarily stopped, the analyzer stops the dispensing of the sample again for a period corresponding to the "setting time" ((2-7) in FIG. 2 and (3-4) in FIG. 3). Although only the dispensing of the sample is temporarily stopped at the timing of (3-2) in FIG. 3, the dispensing of the reagent is also temporarily stopped at the timing of (3-4) in FIG. 3. This state allows the replenishment of the reagent to the reagent disks 41 and/or 42. In other words, during the subsequent "setting time", the operator can replenish the supplemental reagents to the relevant reagent bottles on the reagent disks 41 and/or 42 in accordance with the above-described procedure ((3-4) in FIG. 3).

Figure 5:
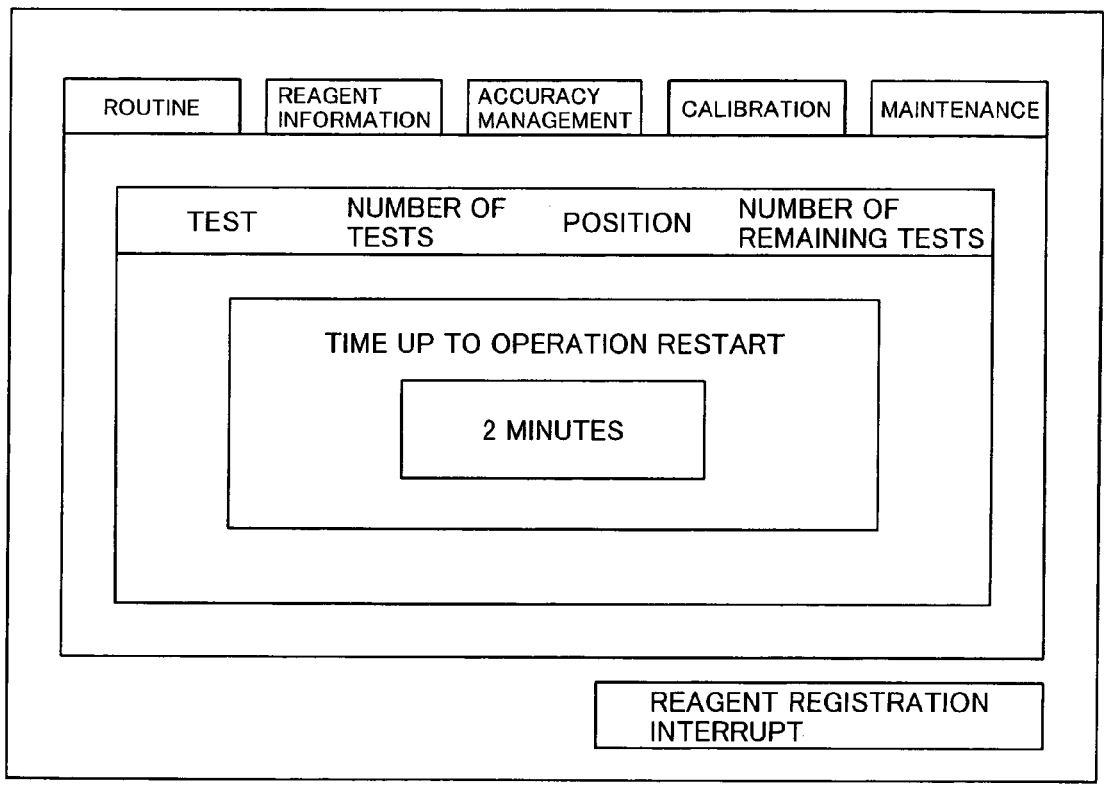
FIG. 5 shows a control screen 2 used in the first embodiment.

Upon reaching the timing at which the replenishment of the reagents is enabled, the analyzer displays a time up to operation restart on the control screen, thus indicating a reagent replenishment allowable time to the operator ((2-8) in FIG. 2 and FIG. 5). Then, after the lapse of the "setting time", the analyzer restarts the analysis (operation) ((2-9) in FIG. 2 and (3-5) in FIG. 3).

An analysis procedure in accordance with a 3-reagent analysis method (i.e., an analysis method of dispensing three kinds of reagents into a sample at a time difference to develop a reaction) will be described below.

A sample to be inspected, e.g., blood, is put in the sample cup 10 and is transported by the transport mechanism 12 while being set on the rack 11. A certain amount of the sample sucked by the sample probe 15 is dispensed into one of the reaction cells 35 arranged on the reaction disk 36, and a certain amount of a first reagent is dispensed into the reaction cell 35 from one of the reagent bottles 40 placed on the reaction disk 41 or 42 by using the reagent probe 21 or 22. The mixture in the reaction cell 35 is then stirred by the stirrer 30 or 31. After the lapse of a predetermined time, a certain amount of a second reagent is dispensed into the reaction cell 35 from another reagent bottle 40 placed on the reaction disk 41 or 42 by using the reagent probe 21 or 22, followed by stirring again by the stirrer 30 or 31. After the lapse of a predetermined time, a certain amount of a third reagent is dispensed into the reaction cell 35 from still another reagent bottle 40 placed on the reaction disk 41 or 42 by using the reagent probe 21 or 22, followed by stirring again by the stirrer 30 or 31.

After the reaction for a predetermined time, the sample absorbance is measured by the optical detector 51, and the measured result is outputted to the control computer 60. If there remains one or more other measurement items requested, the above-described sampling process is repeated. For all the samples set on the rack 11, the sampling process is similarly repeated until all the set measurement items are completed.

One example of a procedure for replenishing reagents during the analysis in the automatic analyzer of this embodiment will be described below with reference to FIGS. 4 to 7.

Figure 6:
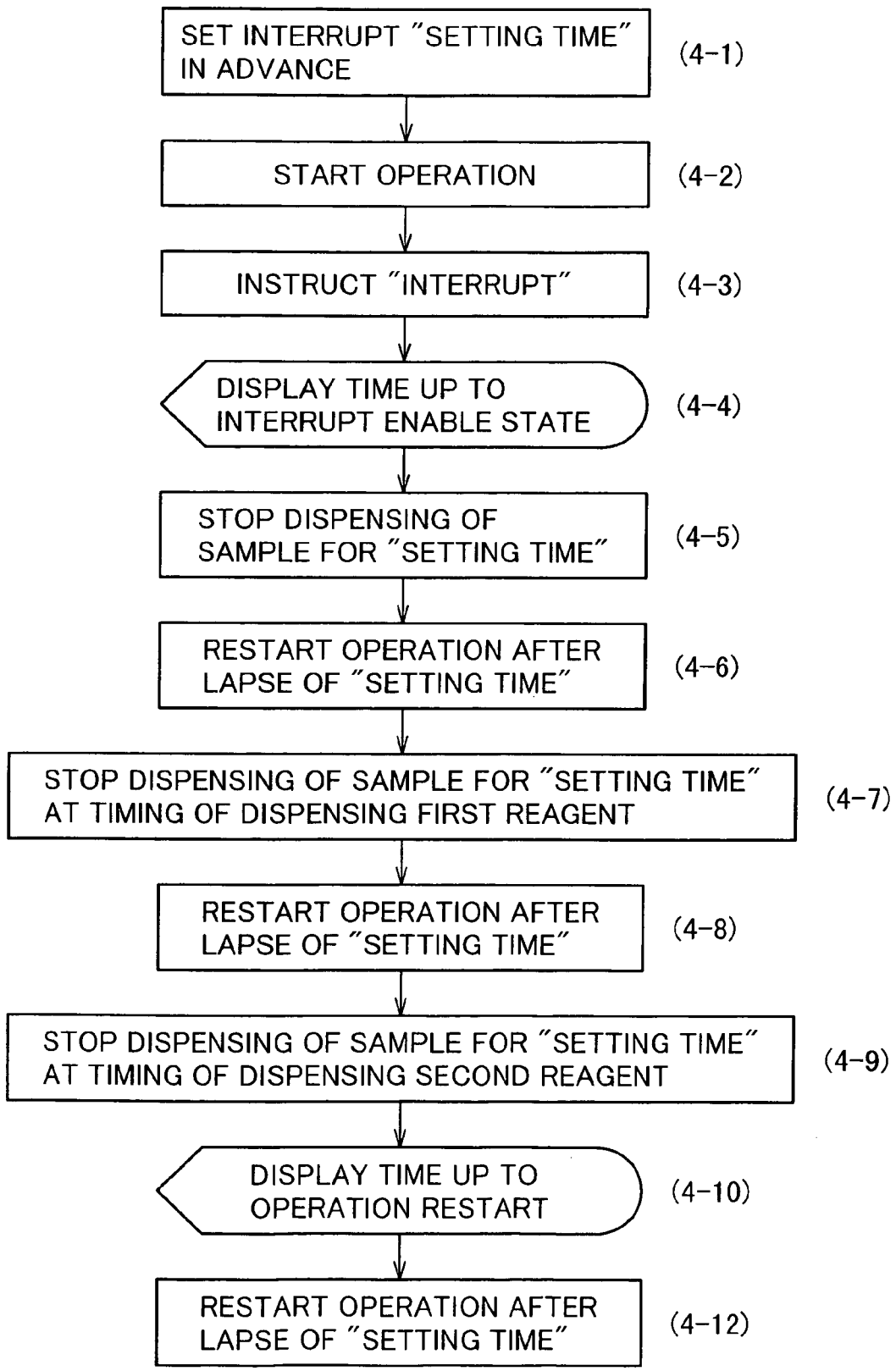
FIG. 6 is a flowchart for replenishing reagents in a 3-reagent analysis according to the first embodiment.

In this example, an interrupt time for replenishing reagents is set before the start of the analysis (operation) ((4-1) in FIG. 6). Note that the setting of the interrupt time is not always required to be registered before the start of the analysis, but the setting may be performed at any desired point in time before the timing of an interrupt for replenishing reagents.

Then, the analysis (operation) is started ((4-2) in FIG. 6). When it is desired to replenish one or more reagents during the analysis, the operator depresses the "reagent registration interrupt" button on the analyzer control screen, thereby issuing the "interrupt" command ((4-3) in FIG. 6 and FIG. 4). The button for issuing the "interrupt" command is not always required to locate on the control screen, but it may be disposed on the analyzer. In response to the button depression, the analyzer temporarily stops the dispensing of the sample for the preset "setting time" (sampling stop state) as indicated by (4-5) in FIG. 6. Simultaneously, the analyzer displays a time up to the timing at which the replenishment of the reagents will be enabled (FIG. 4).

Figure 7:
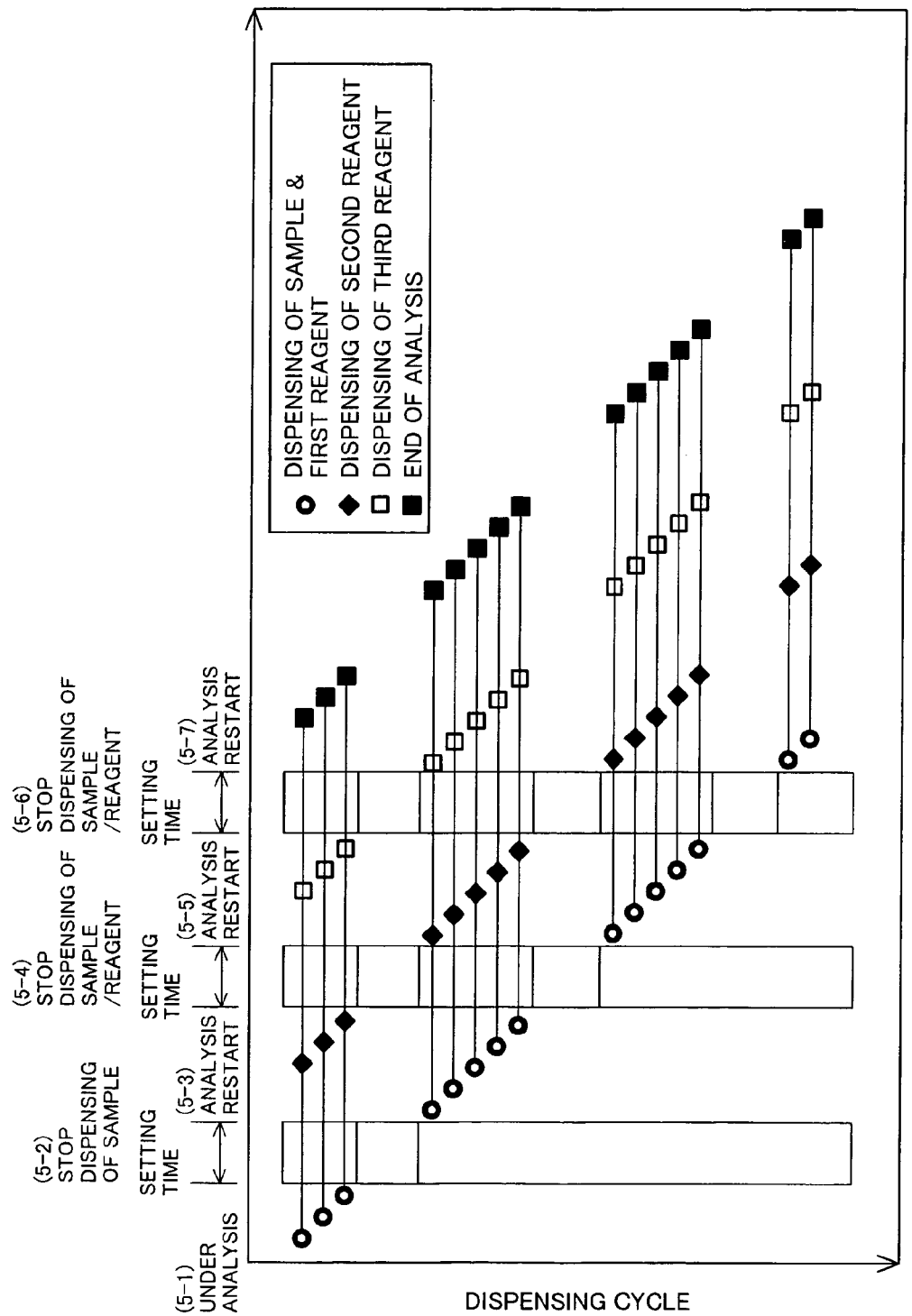
FIG. 7 shows a procedure for dispensing a sample and reagents in the 3-reagent analysis according to the first embodiment.

After the lapse of the "setting time", the analyzer restarts the dispensing of the sample ((4-6) in FIG. 6 and (5-3) in FIG. 7). Subsequently, at the timing in the dispensing of the second reagent corresponding to the timing at which the dispensing of the sample was temporarily stopped, the analyzer stops the dispensing of the sample again for a period corresponding to the "setting time" ((4-7) in FIG. 6 and (5-4) in FIG. 7). Although only the dispensing of the sample is temporarily stopped at the timing of (5-2) in FIG. 7, the dispensing of the second reagent is also temporarily stopped at the timing of (5-4) in FIG. 7.

After the lapse of the "setting time", the analyzer restarts the dispensing of the sample ((4-8) in FIG. 6 and (5-5) in FIG. 7). Subsequently, at the timing in the dispensing of the third reagent corresponding to the timing at which the dispensing of the sample was temporarily stopped, the analyzer stops the dispensing of the sample again for a period corresponding to the "setting time" ((4-9) in FIG. 6 and (5-6) in FIG. 7). Although only the dispensing of the sample and the dispensing of the second reagent are temporarily stopped at the timing of (5-4) in FIG. 7, not only the dispensing of the sample, but also the dispensing of the first and third reagents are temporarily stopped at the timing of (5-6) in FIG. 7. This state allows the replenishment of the reagent to the reagent disks 41 and/or 42. In other words, during the subsequent "setting time", the operator can replenish the supplemental reagents to the relevant reagent bottles on the reagent disks 41 and/or 42 in accordance with the above-described procedure ((5-6) in FIG. 7).

Upon reaching the timing at which the replenishment of the reagents is enabled, the analyzer displays a time up to operation restart on the control screen, thus indicating a reagent replenishment allowable time to the operator ((4-10) in FIG.

6 and FIG. 5). Then, after the lapse of the "setting time", the analyzer restarts the analysis (operation) ((4-11) in FIG. 6 and (5-7) in FIG. 7).

Figure 8:
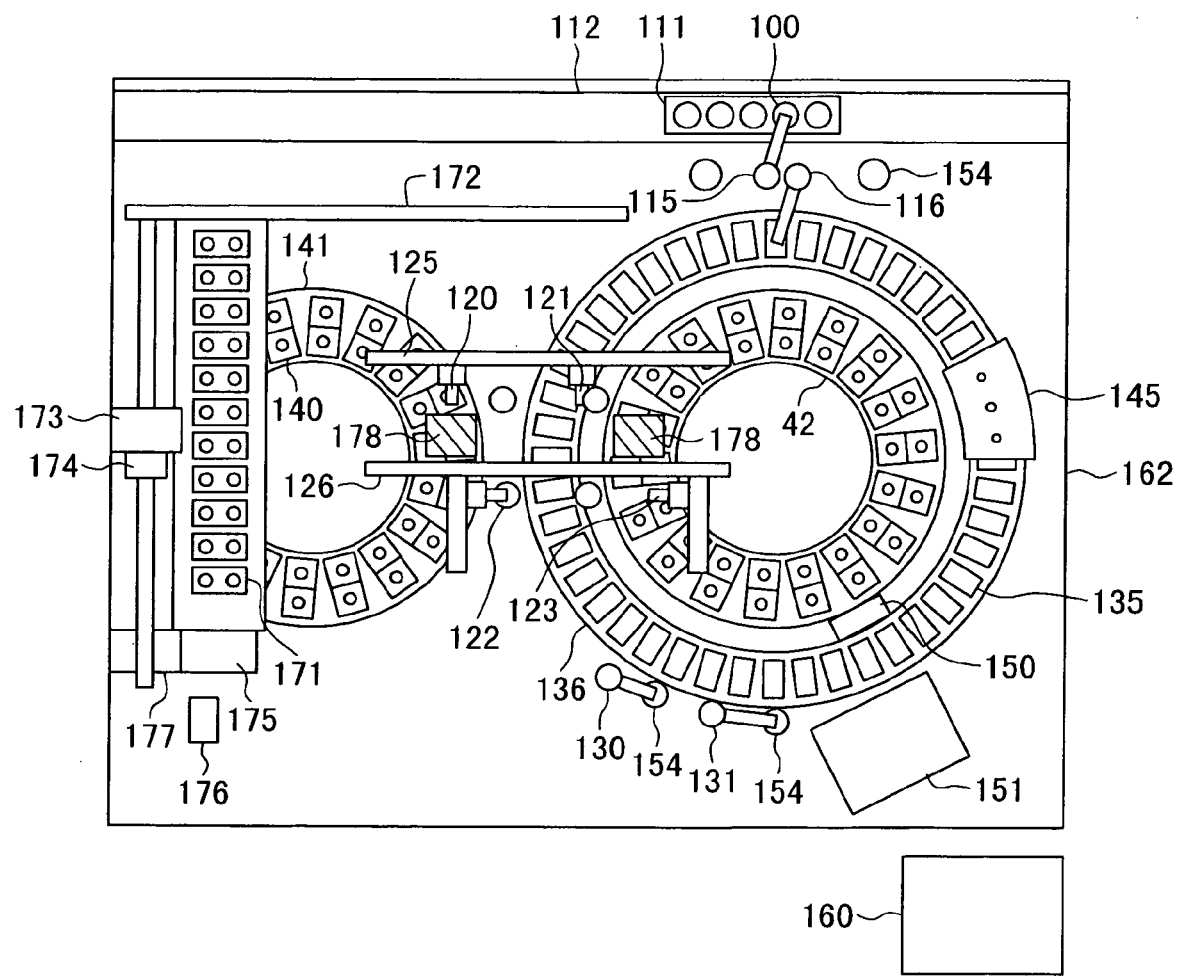
FIG. 8 is a plan view of an automatic analyzer according to a second embodiment of the present invention.

FIG. 8 is a-plan view of an automatic analyzer according to a second embodiment of the present invention.

The second embodiment differs from the first embodiment in including a reagent storage 171 for replenishment so that reagents can be automatically replenished during the analysis. The reagent storage 171 for replenishment is installed above a reagent disk 141. A plurality of reagent bottles 140 can be placed on the reagent storage 171 for replenishment. A rail 172 is disposed to extend over the reagent storage 171 for replenishment, and a reagent holding mechanism 173 and a reagent uncapping mechanism 174 both capable of moving in the 3-axis directions with respect to the rail 172 are mounted to the rail 172. A reagent bottle setting port 175 is provided at a front end of the reagent storage 171 for replenishment. A barcode reader 176 for reading a reagent barcode is disposed near the reagent bottle setting port 175. A disposal port 177 allowing reagent bottle caps and the used reagent bottles 140 to be discarded therethrough is disposed near the reagent storage 171 for replenishment. A sample pump, a reagent pump, a cleaning pump (all of these pumps being not shown), an optical detector 151, reaction cells 135, a reagent disk 141, reagent probes 120, 121, 122 and 123, sample probes 115, 116, the reagent holding mechanism 173, the reagent uncapping mechanism 174, and the barcode reader 176 are connected to a control computer 160.

A procedure for registering reagents in the second embodiment will be described below.

Respective reagents in the reagent bottles 140 placed on the reagent disks 141, 142 are checked. Information of each reagent bottle 140 contains the position where the reagent bottle is placed in the reagent disk 141 or 142, the lot, the expiry date, the amount of the remaining reagent, etc., and is stored in the control computer 160. Based on the information stored in the control computer 160, the operator checks the states of the reagent bottles 140 placed on the reagent disks 141, 142. The reagent bottle in which the reagent remains in small amount and will possibly run out during the analysis in that day is set in the reagent bottle setting port 175. The barcode reader 176 reads the reagent information of the set reagent bottle, following which the set reagent bottle is transported to the reagent storage 171 for replenishment by the reagent holding mechanism 173. The read reagent information and the position of the transported reagent bottle where it is placed in the reagent storage 171 for replenishment are outputted to the control computer(not shown). The reagent bottles for which the reagents are estimated to run out are all checked and transported in accordance with the above-described procedure. Further, a reagent bottle containing a reagent that is required for a special item and used at a very low frequency is also placed in the reagent storage 171 for replenishment in accordance with the above-described procedure.

One example of a procedure for replenishing reagents during the analysis in the automatic analyzer of this embodiment will be described below. The following example is described in connection with a 2-reagent analysis, but it is similarly applicable to a 3-reagent analysis as well.

The analyzer monitors the reagent amount in each reagent bottle during the analysis. When the analyzer detects that the reagent amount has reduced to an insufficient level, it temporarily stops the dispensing of the sample for the preset "setting time" ((3-2) in FIG. 3), followed by restarting the analysis after the predetermined time. Namely, after the lapse of the "setting time", the analyzer restarts the dispensing of the sample ((3-3) in FIG. 3). Subsequently, at the timing in the dispensing of the second reagent corresponding to the timing at which the dispensing of the sample was temporarily stopped, the analyzer stops the dispensing of the sample again for a period corresponding to the "setting time" ((3-4) in FIG. 3). Although only the dispensing of the sample is temporarily stopped at the timing of (3-2) in FIG. 3, the dispensing of the reagent is also temporarily stopped at the timing of (3-4) in FIG. 3. This state allows the replenishment of the reagent to the reagent disks 141 and/or 142. In other words, during the subsequent "setting time", the analyzer automatically transports one or more reagent bottles 140 to the reagent disks 141 and/or 142 from the reagent storage 171 for replenishment, whereby the analysis can be avoided from stopping.

What is claimed is:

1. An automatic analyzer comprising:
   a reaction cell for mixing a sample and at least one reagent therein;
   sample dispensing means for dispensing the sample into said reaction cell;
   reaction cell carrying means for holding a plurality of said reaction cell in plural number along a circumference of a disk and rotating said disk for carrying said reaction cells successively at constant timing;
   at least one reagent table for holding a plurality of reagent bottles;
   reagent dispensing means for performing reagent dispensing operations including drawing a first reagent from a first reagent bottle and injecting the first reagent into said reaction cell on said reaction cell carrying means, and drawing a second reagent from a second reagent bottle and injecting the second reagent into said reaction cell at a predetermined timing of second reagent injection;
   an optical detector for measuring the absorbance of a sample in said reaction cell arranged on said disk;
   a reagent bottle setting port on which a reagent bottle is placed for replenishment;
   a replenishment reagent storage on which reagent bottles are arranged for replenishment,
   a reagent holding mechanism for transporting a reagent bottle among said reagent table, said reagent bottle setting port and said replenishment reagent storage; and
   control means for controlling said sample dispensing means, said reagent dispensing means and said reagent holding mechanism, including stopping the sample dispensing operation of said sample dispensing means at a first stopping time for a preset time period, defined as a time required to perform a reagent replacement operation after said first stopping time and at a predetermined reagent replacement timing to replace said first reagent bottle on said reagent table with a reagent bottle on said replenishment reagent storage, restarting the sample dispensing operation of said sample dispensing means before the predetermined reagent replacement timing, stopping the reagent dispensing operation of said reagent dispensing means at a second stopping time following said predetermined timing of second reagent injection and after the first stopping time of said sample dispensing operation of said sample dispensing means, and restarting the reagent dispensing operation of said reagent dispensing means after the reagent dispensing operation of said reagent dispensing means has been stopped for said preset time period required for the reagent replacement operation,
   said optical detector measuring the absorbance of a sample in said reaction cell and outputting the measured absorbance to the controller, wherein said automatic analyzer transports one of the reagent bottles from said replenishment reagent storage to said reagent table to replace the first reagent bottle on said reagent table with the one reagent bottle on said replenishment reagent storage, during said preset time period which begins at said second stopping time.

2. An automatic analyzer according to claim 1, further comprising a plurality of said reagent dispensing means.

3. An automatic analyzer according to claim 1, wherein said reaction cell carrying means has a reaction cell carrying path in the form of a closed loop.

4. An automatic analyzer according to claim 1, further comprising a display section for displaying a time remaining until said predetermined reagent replacement timing.

5. An automatic analyzer according to claim 1, further comprising a display section for displaying how much time remains within the preset time required for the reagent replacement operation, when the reagent is replaced.

6. An automatic analyzer according to claim 1, further comprising a reagent replacement timing setting display section for setting said predetermined reagent replacement timing by an operator.

7. An automatic analyzer according to claim 1, further comprising reagent bottle holding means for holding a plurality of reagent bottles, wherein said controller monitors an amount of reagent remaining in each of said reagent bottles held on said reagent bottle holding means, and sets said reagent replacement timing accordingly.

8. An automatic analyzer comprising:
a reaction cell for mixing a sample and at least one reagent therein;
sample dispensing means for dispensing the sample into said reaction cell;
reaction cell carrying means for holding a plurality of said reaction cells in plural number along a circumference of a disk and rotating said disk for carrying said reaction cells successively at constant timing;
at least one reagent table for holding a plurality of reagent bottles;
reagent dispensing means for performing reagent dispensing operations including drawing a first reagent from a first reagent bottle on said reagent table and injecting the first reagent into said reaction cell on said reaction cell carrying means, and drawing a second reagent from a second reagent bottle and injecting the second reagent into said reaction cell at a predetermined timing of second reagent injection;
an optical detector for measuring absorbance of a sample in said reaction cell arranged on said disk;
control means for controlling said sample dispensing means and said reagent dispensing means, including stopping the sample dispensing operation of said sample dispensing means at a first stopping time for a preset time period defined as a time required to perform a reagent replacement operation after said first stopping time and at a predetermined reagent replacement timing to replace said first bottle on said reagent table, restarting the sample dispensing operation of said sample dispensing means before the predetermined reagent replacement timing, stopping the reagent dispensing operation of said reagent dispensing means at a second stopping time following said predetermined timing of second reagent injection and after the first stopping time of said sample dispensing operation of said sample dispensing means, and restarting the reagent dispensing operation of said reagent dispensing means after the reagent dispensing operation of said reagent dispensing means has been stopped for said preset time period required for the reagent replacement operation,
said optical detector measuring absorbance of a sample in said reaction cell and outputting the measured absorbance to the controller; and
a display section for displaying how much time remains within the preset time period required for the reagent replacement operation when the first reagent bottle is replaced.

* * * * *